US010881269B2

(12) United States Patent
Tomii et al.

(10) Patent No.: US 10,881,269 B2
(45) Date of Patent: Jan. 5, 2021

(54) ACTIVATION CONTROL METHOD FOR A BATTERY-POWERED MEDICAL APPARATUS

(71) Applicant: OLYMPUS CORPORATION, Hachioji (JP)

(72) Inventors: Yuichi Tomii, Tokyo (JP); Hidetsugu Takahashi, Tokyo (JP); Katsuhiko Nameta, Tokorozawa (JP); Hirotaka Akiba, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 187 days.

(21) Appl. No.: 16/100,574

(22) Filed: Aug. 10, 2018

(65) Prior Publication Data

US 2019/0000304 A1   Jan. 3, 2019

Related U.S. Application Data

(63) Continuation of application No. PCT/JP2017/011737, filed on Mar. 23, 2017.

(30) Foreign Application Priority Data

Apr. 18, 2016   (JP) .................................. 2016-082933

(51) Int. Cl.
*A61B 1/00*    (2006.01)
*G06F 11/00*   (2006.01)
(Continued)

(52) U.S. Cl.
CPC ...... *A61B 1/00032* (2013.01); *A61B 1/00006* (2013.01); *A61B 1/00022* (2013.01);
(Continued)

(58) Field of Classification Search
CPC ............. G06F 11/1417; G06F 11/1441; G06F 11/1438; G06F 9/4408
See application file for complete search history.

(56) References Cited

U.S. PATENT DOCUMENTS 6,754,818 B1 *  6/2004  Lee ........................ G06F 9/4406
                                                              713/1
6,826,710 B2 * 11/2004  Merkin ............... G06F 11/1417
                                                              713/2
(Continued)

FOREIGN PATENT DOCUMENTS

CN          1567208 A       1/2005
CN        101464804 A       6/2009
(Continued)

OTHER PUBLICATIONS

Jun. 20, 2017 Written Opinion of the International Searching Authority issued in Patent Application No. PCT/JP2017/011737.
(Continued)

*Primary Examiner* — Jonathan D Gibson
(74) *Attorney, Agent, or Firm* — Oliff PLC (57) ABSTRACT

A battery-powered medical apparatus including a first memory configured to store a first program, a second memory configured to store a second program, which is different than the first program, and a processor. The processor executes activation of the battery-powered medical apparatus by executing the first program stored in the first memory in response to receiving an activation instruction. In response to the activation failing to complete within a first predetermined period of time, the processor switches from the first program to the second program, and executes the activation of the battery-powered medical apparatus by executing the second program stored in the second memory. The processor then stops power supply from a battery in
(Continued)

response to the activation executed by the second program failing to complete within a second predetermined period of time.

9 Claims, 9 Drawing Sheets

(51) Int. Cl.
*G06F 21/50* (2013.01)
*A61B 1/045* (2006.01)
*A61B 1/06* (2006.01)
*G02B 23/24* (2006.01)

(52) U.S. Cl.
CPC ...... *A61B 1/00039* (2013.01); *A61B 1/00052* (2013.01); *A61B 1/045* (2013.01); *A61B 1/0661* (2013.01); *G06F 21/50* (2013.01); *A61B 1/0002* (2013.01); *A61B 1/00034* (2013.01); *G02B 23/2476* (2013.01)

(56) References Cited

U.S. PATENT DOCUMENTS

| | | | | |
|---|---|---|---|---|
| 7,340,638 | B2* | 3/2008 | Nicholson | G06F 11/0709 714/2 |
| 2003/0051127 | A1* | 3/2003 | Miwa | G06F 9/4406 713/2 |
| 2004/0153724 | A1* | 8/2004 | Nicholson | G06F 11/0709 714/6.11 |
| 2004/0153733 | A1* | 8/2004 | Lin | G06F 11/1417 714/6.12 |
| 2004/0172578 | A1* | 9/2004 | Chen | G06F 11/1417 714/15 |
| 2010/0205423 | A1* | 8/2010 | Shao | G06F 11/1417 713/2 |
| 2010/0213891 | A1* | 8/2010 | Nishikawa | H01M 10/42 320/106 |
| 2013/0283030 | A1* | 10/2013 | Drew | G06F 9/448 713/100 |
| 2014/0293691 | A1* | 10/2014 | Arakawa | G11C 16/30 365/185.08 |
| 2014/0365823 | A1* | 12/2014 | Michihata | G06F 11/1441 714/16 |
| 2015/0121358 | A1* | 4/2015 | Nekoomaram | H04L 67/10 717/170 |
| 2019/0000304 | A1* | 1/2019 | Tomii | A61B 1/00022 |

FOREIGN PATENT DOCUMENTS

| | | |
|---|---|---|
| JP | 2003-084979 A | 3/2003 |
| JP | 2005-222366 A | 8/2005 |
| JP | 2014-003472 A | 1/2014 |
| JP | 2015-112154 A | 6/2015 |

OTHER PUBLICATIONS

Jun. 20, 2017 International Search Report issued in Patent Application No. PCT/JP2017/011737.

Nov. 21, 2017 Office Action issued in Japanese Patent Application No. 2017-553434.

Apr. 3, 2018 Office Action issued in Japanese Patent Application No. 2017-553434.

Oct. 21, 2019 Office Action issued in Chinese Patent Application No. 201780007206.9.

* cited by examiner

|       | SEL (0) | SEL (1) | ---- | SEL (N) |
|-------|---------|---------|------|---------|
| ROM a | 1       | 0       | ---- | 0       |
| ROM b | 0       | 1       | ---- | 0       |
| ⋮     | ----    | ----    | ---- | ----    |
| ROM x | 0       | 0       | ---- | 1       |

ACTIVATION CONTROL METHOD FOR A BATTERY-POWERED MEDICAL APPARATUS

CROSS-REFERENCE TO RELATED APPLICATIONS

This application is a Continuation application of PCT Application No. PCT/JP2017/011737, filed Mar. 23, 2017 and based upon and claiming the benefit of priority from prior Japanese Patent Application No. 2016-82933, filed Apr. 18, 2016, the entire contents of all of which are incorporated herein by reference.

BACKGROUND

Field of the Invention

The present embodiments are related to a battery-powered medical apparatus.

Description of the Related Art

The number of medical apparatuses controlled through a computer software process is on the increase. The control program of such an apparatus is updated so as to expand the functions or to respond to past faults.

While updating is a useful function, a fault occurs during updating on rare occasions. In response to this, a mobile terminal device is proposed that has two sets of program codes so that it can be activated even when a fault has occurred during the update of a program (Japanese Laid-open Patent Publication No. 2014-3472 for example).

SUMMARY

The battery-powered medical apparatus according to the present embodiment is a battery-powered medical apparatus including a first memory configured to store a first program, a second memory configured to store a second program, which is different than the first program, and a processor configured to: (i) execute activation of the battery-powered medical apparatus by executing the first program stored in the first memory in response to receiving an activation instruction, (ii) in response to the activation of the battery-powered medical apparatus failing to complete within a first predetermined period of time from start of executing activation by the first program, switch a program from the first program to the second program, and execute the activation of the battery-powered medical apparatus by executing the second program stored in the second memory, and (iii) control power supply from a battery to stop the power supply from the battery to the battery-powered medical apparatus in response to the activation executed by the second program failing to complete within a second predetermined period of time after executing the activation by the second program.

DETAILED DESCRIPTION OF THE EMBODIMENTS

Hereinafter, explanations will be given for the embodiments by referring to the drawings. The present embodiments are related to a battery-powered medical apparatus. The battery-powered medical apparatus is for example a battery-powered endoscopic apparatus or a battery-powered surgical operation apparatus used for endoscopic examinations in medical facilities (hospitals etc.). Hereinafter, explanations will be given by using a battery-powered endoscopic apparatus as an example of a battery-powered medical apparatus.

Figure 1:
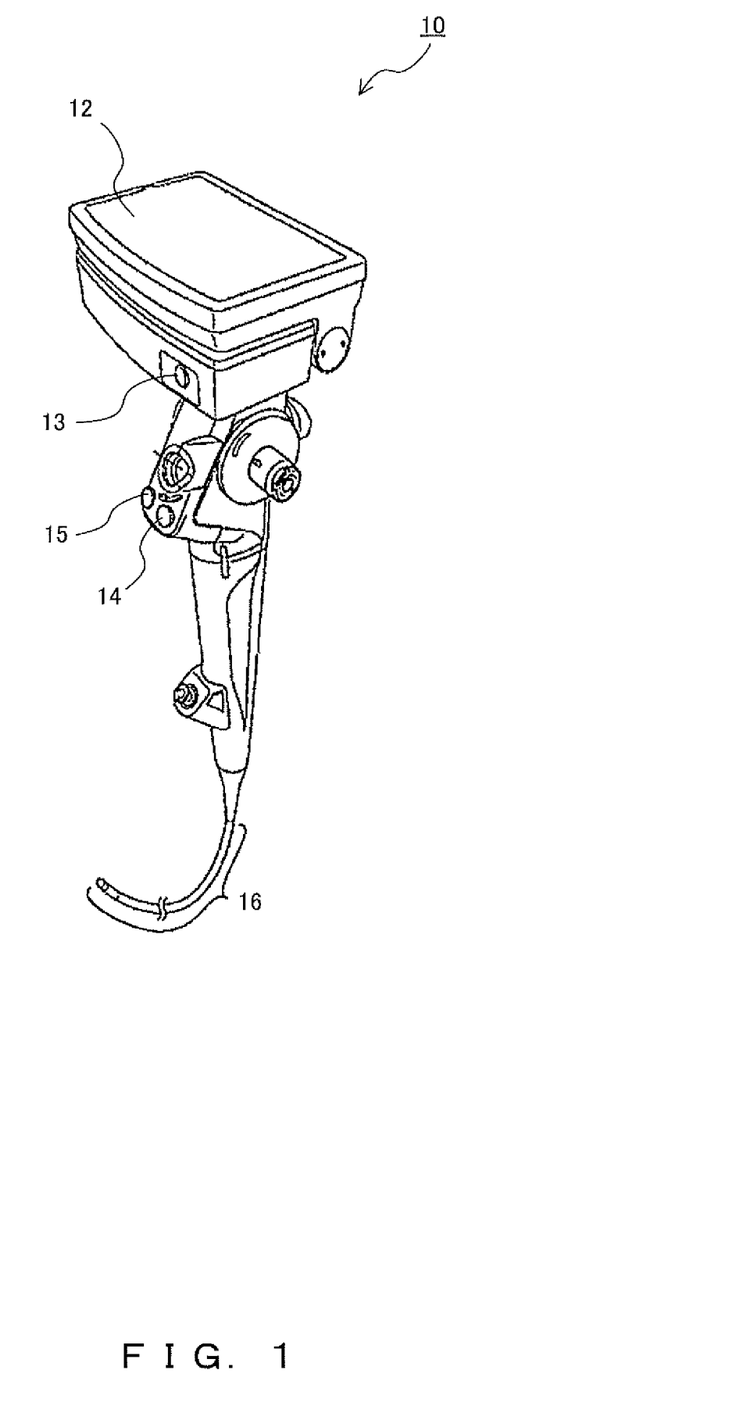
FIG. 1 illustrates an example of an external configuration of a battery-powered endoscopic apparatus according to the present embodiment.

FIG. 1 illustrates an example of an external configuration of a battery-powered endoscopic apparatus 10 (which will be referred to as the endoscope 10) according to the present embodiment. As illustrated in FIG. 1, the endoscope 10 according to the present embodiment includes a liquid crystal display (LCD) 12 with a touch panel and a power button 13 in the upper portion. The endoscope 10 includes a shooting-mode button 14 and a release button 15 in the middle portion, and includes an insertion unit 16 in the lower portion.

The LCD 12 with a touch panel has a function as a monitor for displaying an image to be observed, various types of information, etc., and also has a function as a manipulation unit for receiving various types of instructions and manipulations from the user (doctor etc.). The power button 13 is a button for giving an instruction to turn on or turn off the power of the endoscope 10.

The shooting-mode button 14 is a button for giving an instruction to switch the shooting mode. In more detail, the shooting-mode button 14 is a button for giving an instruction to switch from the still-image-shooting mode to the video-image-shooting mode or an instruction to switch from the video-image-shooting mode to the still-image-shooting mode. The release button 15 is a button for giving an instruction about still-image shooting during the still-image-shooting mode, an instruction to start or terminate video-image shooting during the video-image-shooting mode, or other instructions. The power button 13, the shooting-mode button 14, and the release button 15 are mechanical switches.

Figure 2:
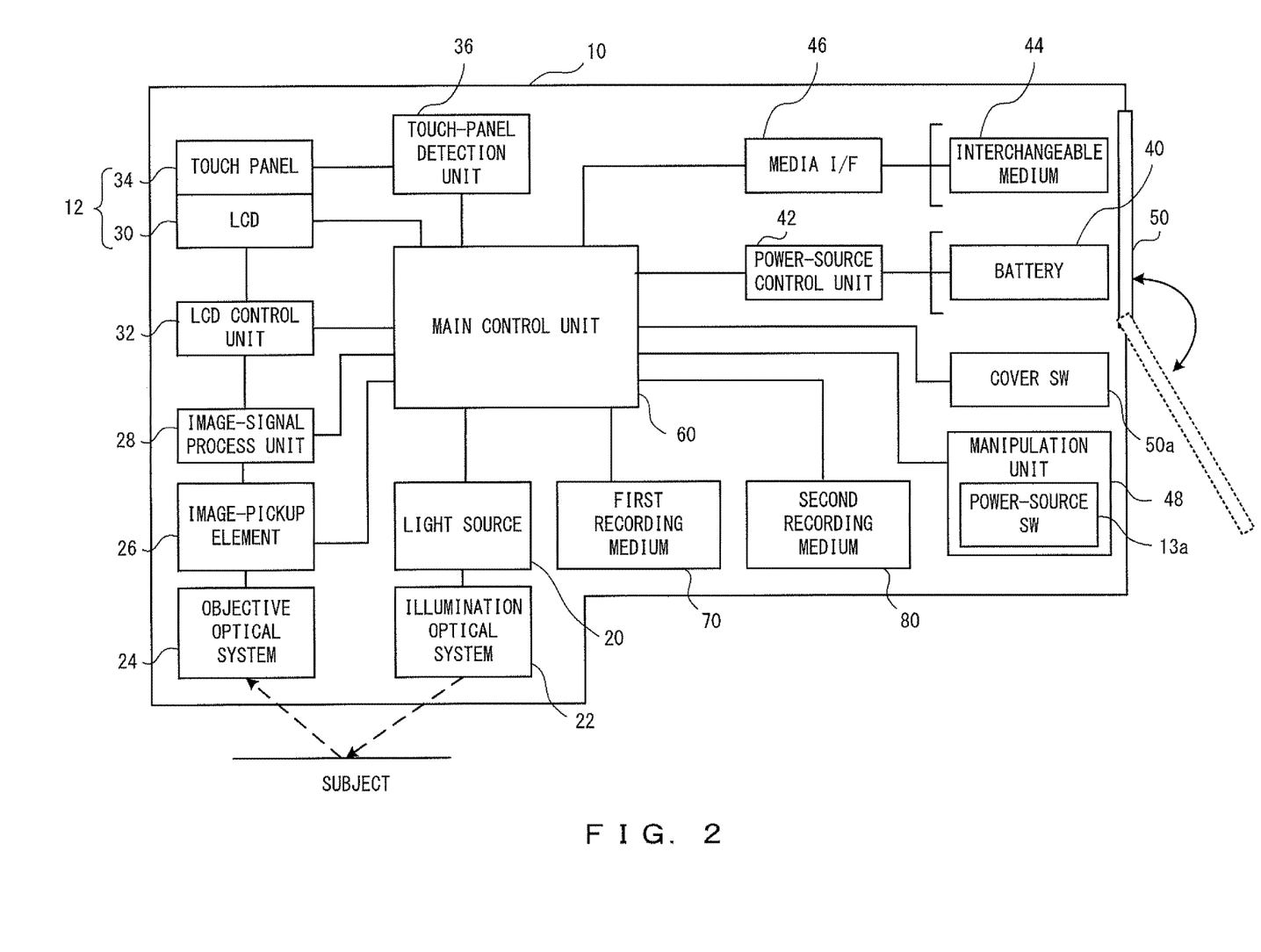
FIG. 2 illustrates an example of a system configuration of the endoscope according to the present embodiment.

The insertion unit 16 is a portion of the endoscope 10 that is to be inserted into the site to be examined in the body cavity, which serves as an examination subject, and includes a hard tip portion and other portions that are soft (soft sections). FIG. 2 illustrates an example of a system configuration of the endoscope 10 according to the present embodiment. The endoscope 10 includes a light source 20, an illumination optical system 22, an objective optical system 24, an image-pickup element 26, an image-signal process unit 28, an LCD control unit 32, the LCD 12 with a touch panel (an LCD 30 and a touch panel 34), and a touch-panel detection unit 36.

The light source 20 is for example a semiconductor light source, and emits illumination light. The illumination optical system 22 guides the illumination light, emitted from the light source 20, to a light guide fiber (not illustrated), and illuminates the subject (the site to be examined in the body cavity, which serves as the examination subject).

The objective optical system 24 forms an image on the image-pickup plane of the image-pickup element 26 from the light reflected from the subject that is illuminated with the illumination light. The image-pickup element 26 is an image sensor such as a Charge-Coupled Device (CCD), a Complementary Metal Oxide Semiconductor (CMOS), etc., and converts the subject image formed on the image-pickup plane (light reflected from the subject) into an image signal as an electric signal. The image-signal process unit 28 performs a prescribed process on the image signal obtained by the image-pickup element 26. The LCD 30 displays an image (a still image or a video image) in accordance with the image signal processed by the image-signal process unit 28, various types of information, manipulation buttons, etc. The LCD control unit 32 controls the LCD 30 so as to make the LCD 30 display various types of information.

The LCD 12 with a touch panel includes the LCD 30 and the touch panel 34, and employs a configuration in which the LCD 30 is provided with the touch panel 34. The touch panel 34 receives various types of instructions and manipulations from the user. The touch-panel detection unit 36 detects where and how the user touches the touch panel 34.

The endoscope 10 also includes a battery 40, a power-source control unit 42, an interchangeable medium 44, a media I/F 46, a manipulation unit 48, a cover 50, and a cover SW 50a. The battery 40 is a secondary battery that supplies electric power to the endoscope 10, and is for example a lithium-ion battery or a nickel hydride battery. The battery 40 is removable from the endoscope 10. The power-source control unit 42 controls the power from the battery 40, and converts the power from the battery 40 into a prescribed voltage so as to supply the voltage to the respective units in the endoscope 10.

The interchangeable medium 44 is a non-volatile recording medium mainly for recording picked up images, and is removable from the endoscope 10. The interchangeable medium 44 is for example an SD card. The media I/F (Interface) 46 relays data with the internal portion when the data is recorded in the interchangeable medium 44 or is reproduced.

Note that the interchangeable medium 44 may store an update program so as to update a program. The update of a program performed by using the interchangeable medium 44 will be described later.

The manipulation unit 48 includes the power-source SW 13a corresponding to the power button 13, and reports manipulations on each switch to the main control unit 60, which will be described later. Note that the power-source SW 13a is connected to a power-source control unit 42, which will be described for FIG. 3. The cover 50 seals the storage chamber (not illustrated) for storing the battery 40 and the interchangeable medium 44. This is because the endoscope 10 has to undergo washing, disinfection, sterilization, etc. before and after being used. The cover 50 waterproofs the inside of the storage chamber, and thereby protects the interchangeable medium 44 and the battery 40 from the disinfectant etc. The cover SW 50a detects the opening and closing of the cover 50 to report the detected result to the main control unit 60. The dotted lines depict the cover 50 in the opened state.

The endoscope 10 further includes the main control unit 60, a first recording medium 70, and a second recording medium 80. The main control unit 60 includes a processor, and entirely controls the endoscope 1 through a software process executed by the processor that has read a program. For example, the main control unit 60 controls the respective units so that the units perform processes such as image-pickup etc. in accordance with a manipulation detected by the touch-panel detection unit 36 or a manipulation received by the manipulation unit 48.

The first recording medium 70 is a non-volatile recording medium that stores a control program read by the processor. The first recording medium 70 is for example a flash memory or an EEPROM. The type and the configuration of the first recording medium 70 will be explained later.

The second recording medium 80 is a non-volatile recording medium that mainly records picked up images together with the interchangeable medium 44. The second recording medium 80 is for example a flash memory. Specifically, the second recording medium 80 records image data (still image data or video image data) in accordance with an image signal processed by the image-signal process unit 28, various types of information, etc.

Note that the endoscope 1 configured as above may employ the following configuration. While the endoscope 10 has the image-pickup function as an integrated element, the image-pickup function may be configured to be removable as a camera unit. In such a case, the endoscope 10 may include for example the camera unit that is removable from the eye piece provided to the endoscope. Further, in such a case, the endoscope having that eye piece may be for example a fiber scope that transmits an optical image through an optical fiber or may be a rigid scope that transmits an optical image by a relay lens. Also, the subject may be illuminated in a simultaneous method, a frame sequential method, etc. In this example, simultaneous method refers to a method in which the subject is illuminated with white light, and frame sequential method is a method in which the subject is sequentially illuminated with beams of light in different wavelength bands (beams of light having different color components) in time series.

Also, the light source 20 may be provided to for example the tip portion of the insertion unit 16. Various types of light sources may be used as the light source 20, including for example a white Light Emitting Diode (LED) that emits white light, a light source that uses a plurality of LEDs each emitting a beam of light in a different wavelength band (R, G, B, etc.) to obtain illumination light having a desired color tone by combining beams of light emitted from the respective LEDs, and a laser light source.

Also, the image-pickup element 26 may be provided to for example the tip portion of the insertion unit 16. Also, the touch panel 34 may employ various methods as the detection method including for example a capacitance touch method, a resistive membrane method, an ultrasonic surface acoustic wave method, an optical method (an infrared optical imaging method), and an electromagnetic induction method. Also, while the battery 40 was described to be removable from the endoscope 10, it may be embedded.

First Embodiment

Explanations will be given for an activation process by a program according to the first embodiment by referring to FIG. 3 through FIG. 6. In the first embodiment, the main memory (also referred to as the first storage unit) storing a first program and a sub memory (also referred to as the second storage unit) storing a second program are provided, the sub memory being of the same type as the main memory, and when the activation is impossible through the first program, the memory is switched to the sub memory so that the activation is performed by the second program.

The first program is a program for a normal operation of the endoscope 10. The second program is a program that implements the functions of the first program only partially. For example, the second program implements the activation process and the fundamental functions (image pickup and display process) of the endoscope 10. The second program may include a program for update.

Figure 3:
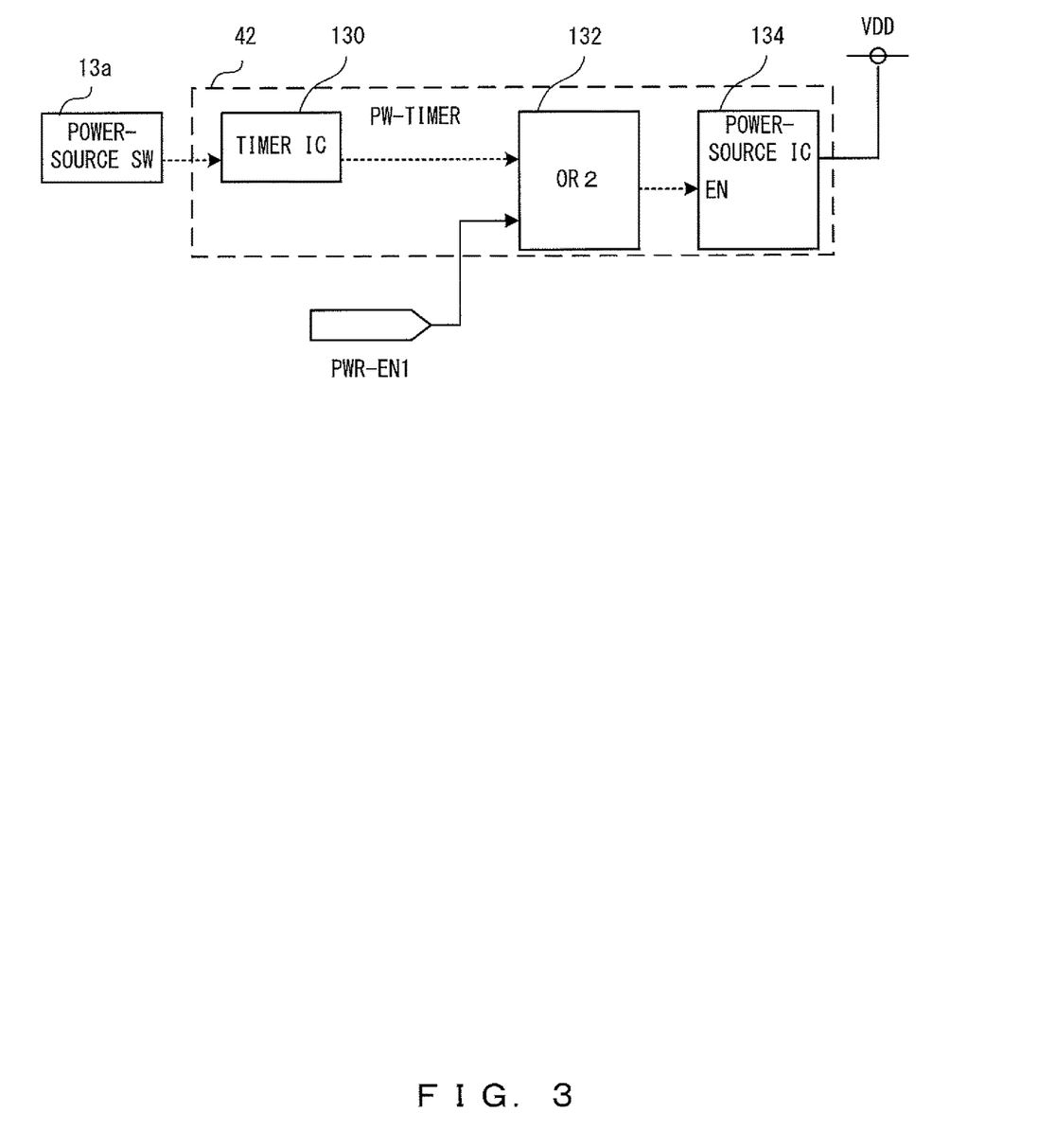
FIG. 3 illustrates an example of a configuration of a power-source control unit according to the first embodiment.
Figure 4:
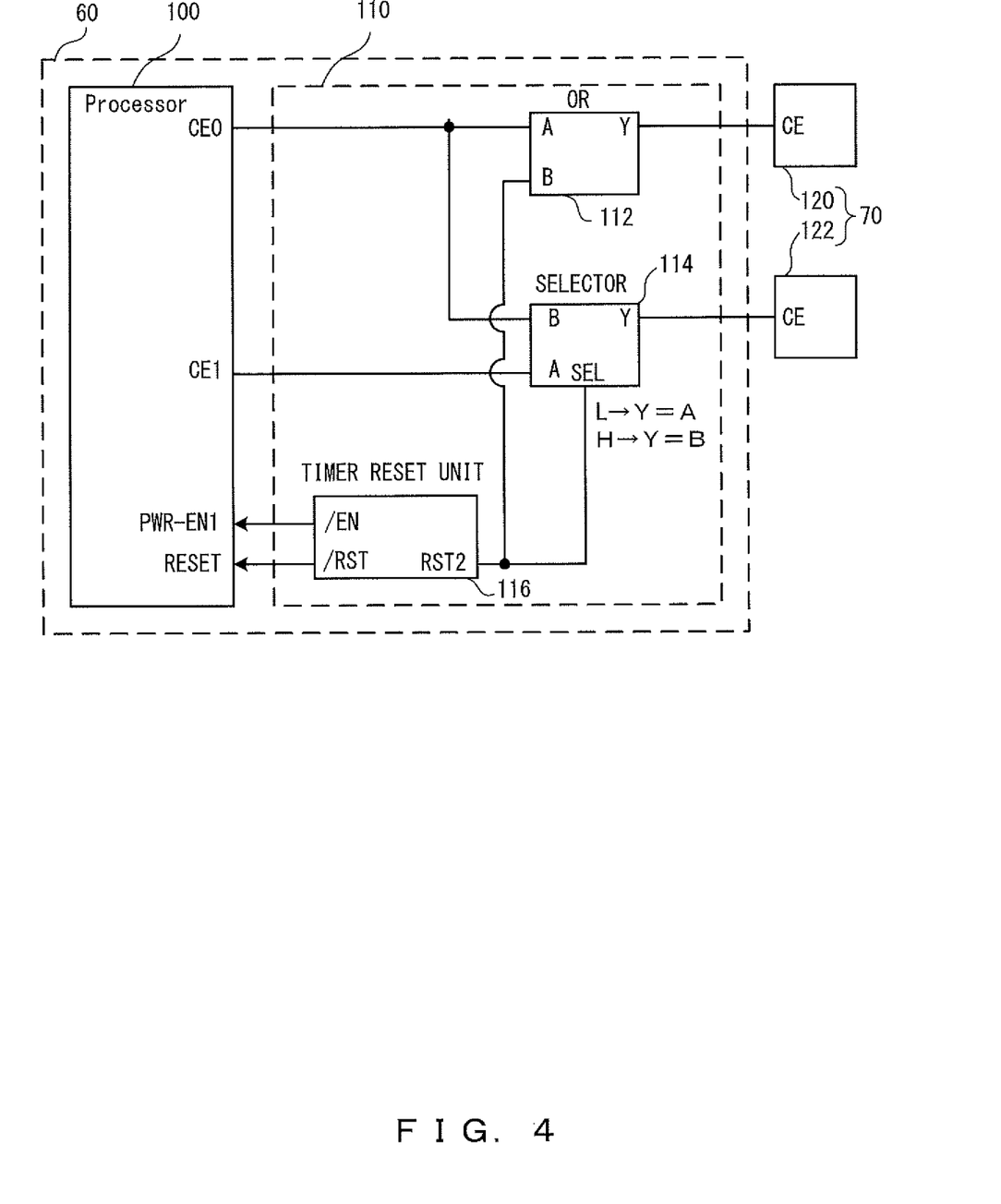
FIG. 4 illustrates an example of a configuration of a main control unit according to the first embodiment.
Figure 5:
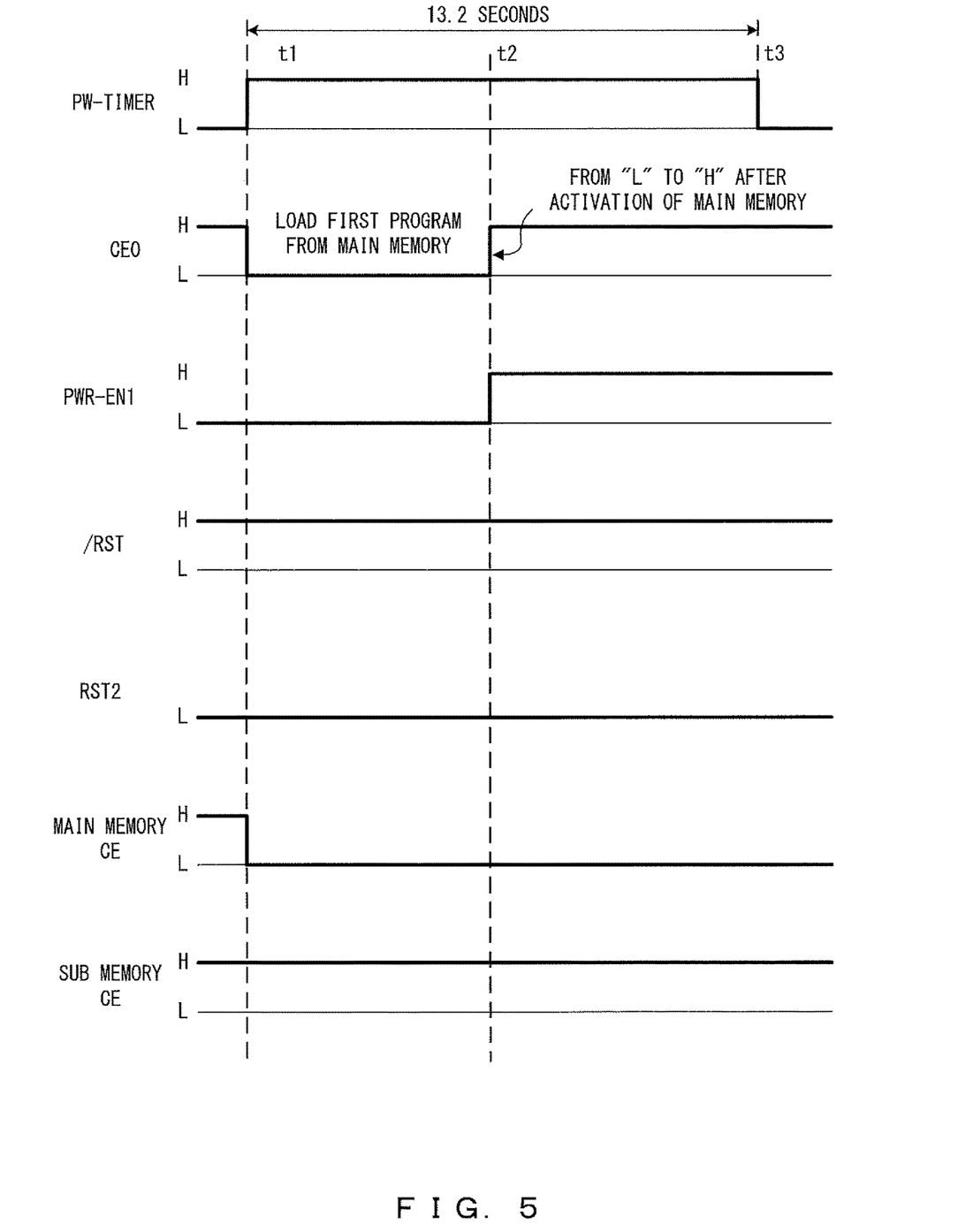
FIG. 5 is a time chart for normal activation according to the first embodiment.
Figure 6:
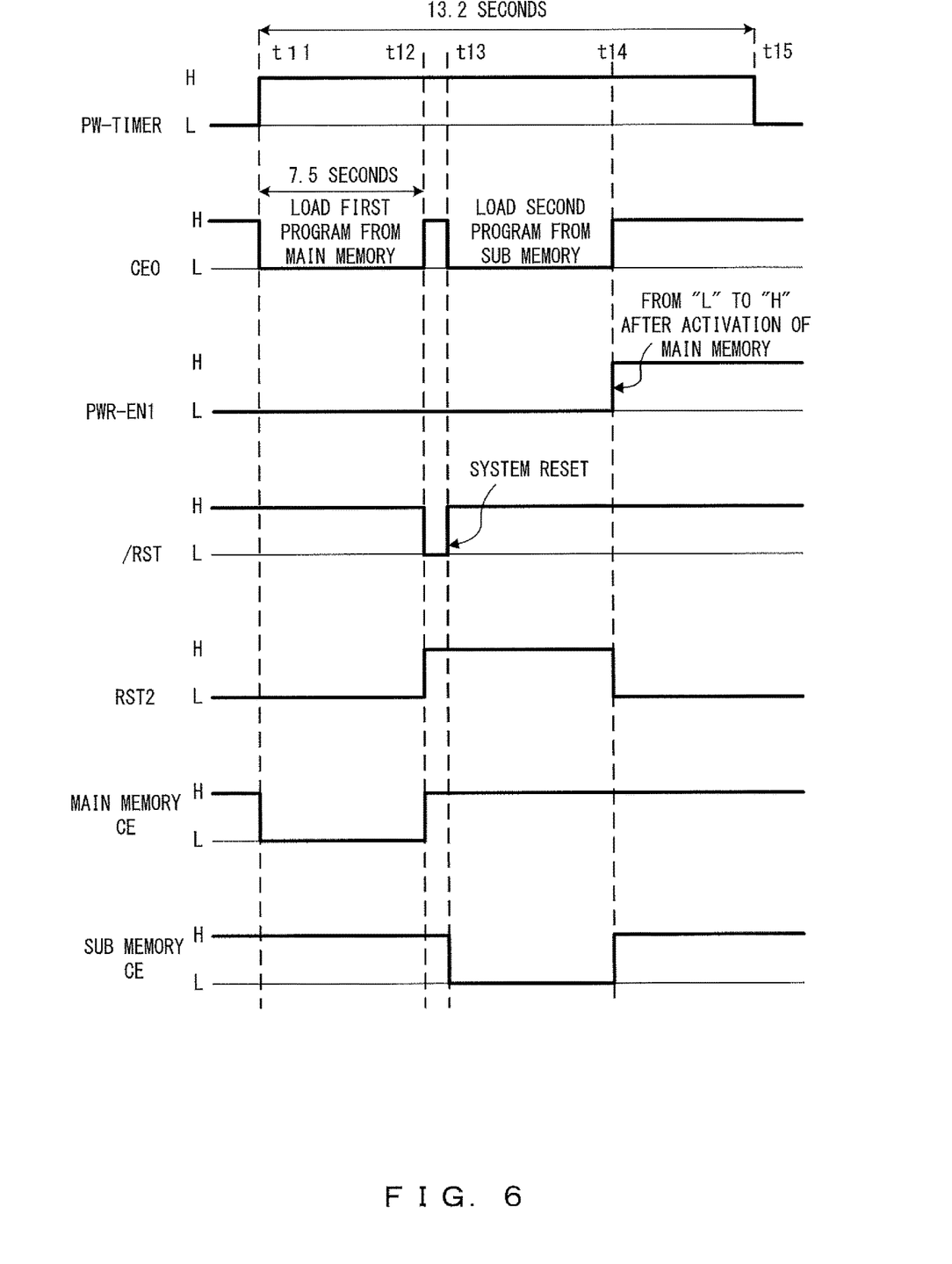
FIG. 6 is a time chart for an activation failure according to the first embodiment.

FIG. 3 illustrates a configuration example of the power-source control unit 42 according to the first embodiment. FIG. 4 illustrates a configuration example of the main control unit 60 according to the first embodiment. FIG. 5 is a time chart for normal activation according to the first embodiment. FIG. 6 is a time chart for an activation failure according to the first embodiment.

FIG. 3 illustrates the power-source control unit 42 including a timer IC 130, an OR2 gate 132, and a power-source IC 134. The timer IC 130 detects that the power-source SW 13a has been turned on, and output "H" as PW-TIMER (power timer signal) for a fixed period of time. When either PW-TIMER from the timer IC 130 or PWR-EN1 (power enable signal) of the processor 100 is "H", the OR2 gate 132 outputs "H" to EN (enable terminal) of the power-source IC 134, and turns on the power-source IC 134. Explanations will be given for the main control unit 60 by referring to FIG. 4. The main control unit 60 according to the first embodiment includes the processor 100 and a memory switching unit 110. The memory switching unit 110 switches between the main memory 120 and the sub memory 122 as the memory for storing a program that is read by the processor 100. The main memory 120 and the sub memory 122 are constituents of the first recording medium 70. An example of the main memory 120 and the sub memory 122 is a NOR-type flash memory.

The memory switching unit 110 includes an OR gate 112, a selector 114, and a timer reset unit 116. The OR gate 112 switches between accesses from the processor 100 to the main memory 120. The selector 114 switches a signal to the chip selector (CE) of the sub memory 122 to the CE0 or the CE1 of the processor 100. Through the selector 114, the value of A is output to Y when SEL is "L" and the value of B is output to Y when SEL is "H". RST2 of the timer reset unit 116 is output to SEL of the selector 114 and B of the OR gate 112. /RST of the timer reset unit 116 is output to RESET of the processor 100. /EN of the timer reset unit 116 is output to PWR-EN1 of the processor 100. Explanations will be given for the operation performed upon normal activation by referring to FIG. 5. When turning on of the power-source SW 13a is transmitted to the timer IC 130, the timer IC 130 outputs "H" as PW-TIMER to the OR2 gate 132 for a fixed period of time (t1 through t3, 13.2 seconds for example). "H" is output from the OR2 gate 132 to EN of the power-source IC 134, and the power-source control unit 42 turns on the power source.

At the same time, the processor 100 performs control to switch the CE0 from "H" to "L". Also, "L" is output as RST2 from the timer reset unit 116. "L" and "L" are respectively output as the CE0 and RST2 to the OR gate 112, and "L" is output from Y of the OR gate 112 to the CE of the main memory 120. The CE of the main memory 120 is turned from "H" to "L", and the main memory 120 enters a selected state.

Also, because RST2 of the timer reset unit 116 is "L", "L" is input to SEL of the selector 114. The CE of the sub memory 122 is maintained at "H", and the sub memory 122 enters a non-selected state. Thereby, the main memory 120 is selected for the processor 100, and the processor 100 loads the first program that has been stored in the main memory 120.

When the first program is normally loaded from the main memory 120, PWR-EN1 of the processor 100 is switched to "H" (the timing at t2 in FIG. 5). Thereby, even when the prescribed period of time (t3, 13.2 seconds) elapses and PW-TIMER is turned to "L", the "ON" state is maintained in the power-source IC 134. Next, explanations will be given for a case where the activation by the use of the first program of the main memory 120 fails. FIG. 6 is a time chart for failure of the activation that uses the first program. As described above, the power-source SW 13a is turned on (t11), and the power-source IC 134 is maintained in an on state for 13.2 seconds (t11 through t15). When a prescribed period of time (which will be also referred to as a first period, and is for example 7.5 seconds) elapses (t12) with the first program failing to achieve normal activation after the power-source IC 134 is turned on, /RST of the timer reset unit 116 is turned from "H" to "L" and RST2 of the timer reset unit 116 is turned from "L" to "H".

"L" of /RST of the timer reset unit 116 is input to RESET of the processor 100, and the processor 100 is reset (system reset) (t13). Also, because RST2 of the timer reset unit 116 is "H", switching is performed so that Y=B in the selector 114. It enters a situation in which the sub memory 122 is controlled by the CE0 of the processor 100. During this, the CE of the main memory 120 is fixed at "H" in OR gate 112, and it enters a situation in which a program is not loaded.

The processor 100 performs control to switch the CE0 from "H" to "L" (t13), and loads the second program that has been stored in the sub memory 122. After loading the second program, when the processor 100 achieves normal activation, the processor 100 switches PWR-EN1 from "L" to "H". This fixes the power-source IC 134 in an on state.

Note that after normal activation through the second program, the processor 100 may read an update program from the second program or the interchangeable medium 44 so as to update the first program in the main memory 120. This remedies a defect of the first program.

When the second program in the sub memory 122 fails to achieve activation also in a prescribed period of time (for example four seconds, t13 through t14), PW-TIMER of the timer IC 130 is switched from "H" to "L" and PWR-EN1 is maintained at "L" in the processor 100. Note that the period of time between t13 and t14 will be also referred to as a second period. Thereby, the output from the OR2 gate 132 to EN of the power-source IC 134 is switched from "H" to "L", and the power-source IC 134 is turned off. This surely enables the prevention of battery consumption because the power source is turned off with the elapse of a fixed period of time when activation is impossible even through the second program.

Second Embodiment

Explanations will be given for an activation process by a program according to the second embodiment by referring to FIG. 7 and FIG. 8. While the first embodiment selects a program from between programs stored in memories of the same type, the second embodiment selects a program from among programs stored in memories of different types.

Figure 7:
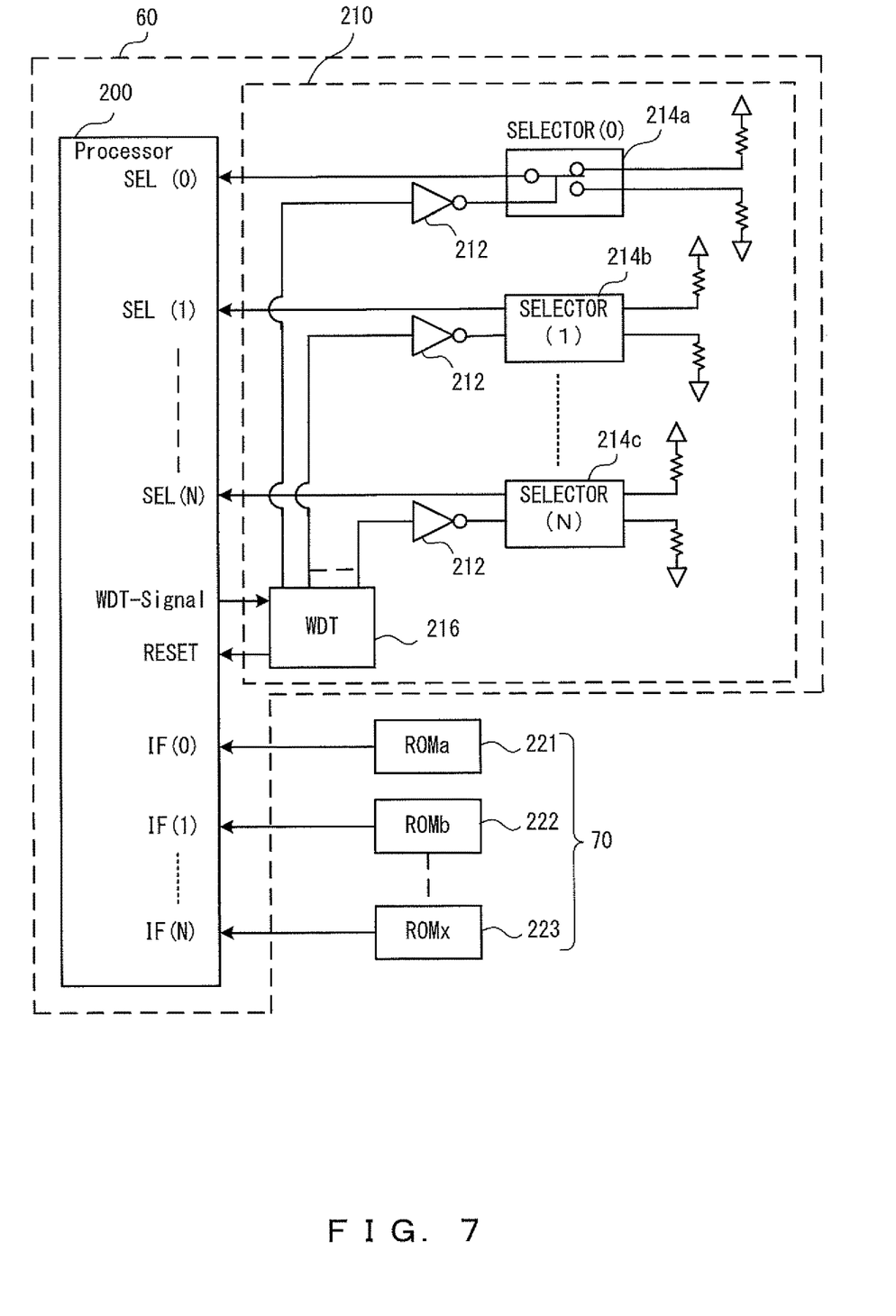
FIG. 7 illustrates an example of a configuration of a main control unit according to the second embodiment.

FIG. 7 illustrates a configuration example of the main control unit 60 according to the second embodiment. Note that the power-source control unit 42 according to the second embodiment has basically the same configuration as that illustrated in FIG. 3 (first embodiment), and thus will not be explained.

The main control unit 60 according to the second embodiment includes a processor 200 and a memory switching unit 210. The memory switching unit 210 includes an inverter 212, a selector 214, and a watchdog timer (WDT) 216.

The processor 200 has a plurality of ROMs connected to its ports in a corresponding manner, the ROMs serving as the first recording mediums 70 each storing programs. In the figure, the ROMs appear as a ROM a221, a ROM b222, . . . , and a ROM x223. The ROM a221, the ROM b222, . . . , and the ROM x223 are connected to IF(0), IF(1), . . . , and IF(N) of the processor 200 in a corresponding manner.

The ROM a221 is treated as a main memory, and the others such as the ROM b222 are treated as sub memories. Specifically, the first program for the normal operation is stored in the ROM a221, which is the main memory (first storage unit). The second program that implements the basic functions (image pickup and display process) is stored in ROMs other than the ROM a221, such as the ROM b222 etc (second storage units). Any types of ROM may be used such as a NOR-type flash memory, a NAND-type flash memory, a PROM, an EEPROM, etc.

The selector 214 switches the memory that is used for the activation in accordance with an instruction from the WDT 216. As many selectors 214 as ROMs are provided. FIG. 7 illustrates a selector (0) 214a, a selector (1) 214b, . . . , a selector (X) 214c as the selectors 214. Each selector 214 has pull-down and pull-up resistors connected to its input terminals. The outputs of each selector 214 are input to terminals (SEL(0), SEL(1), . . . , and SEL(N)) of the processor 200 in a corresponding manner.

The WDT 216 outputs a reset signal to the processor 200 after a prescribed period of time. The WDT 216 also transmits a switching signal to the selectors 214 via inverters 212.

Figure 8:
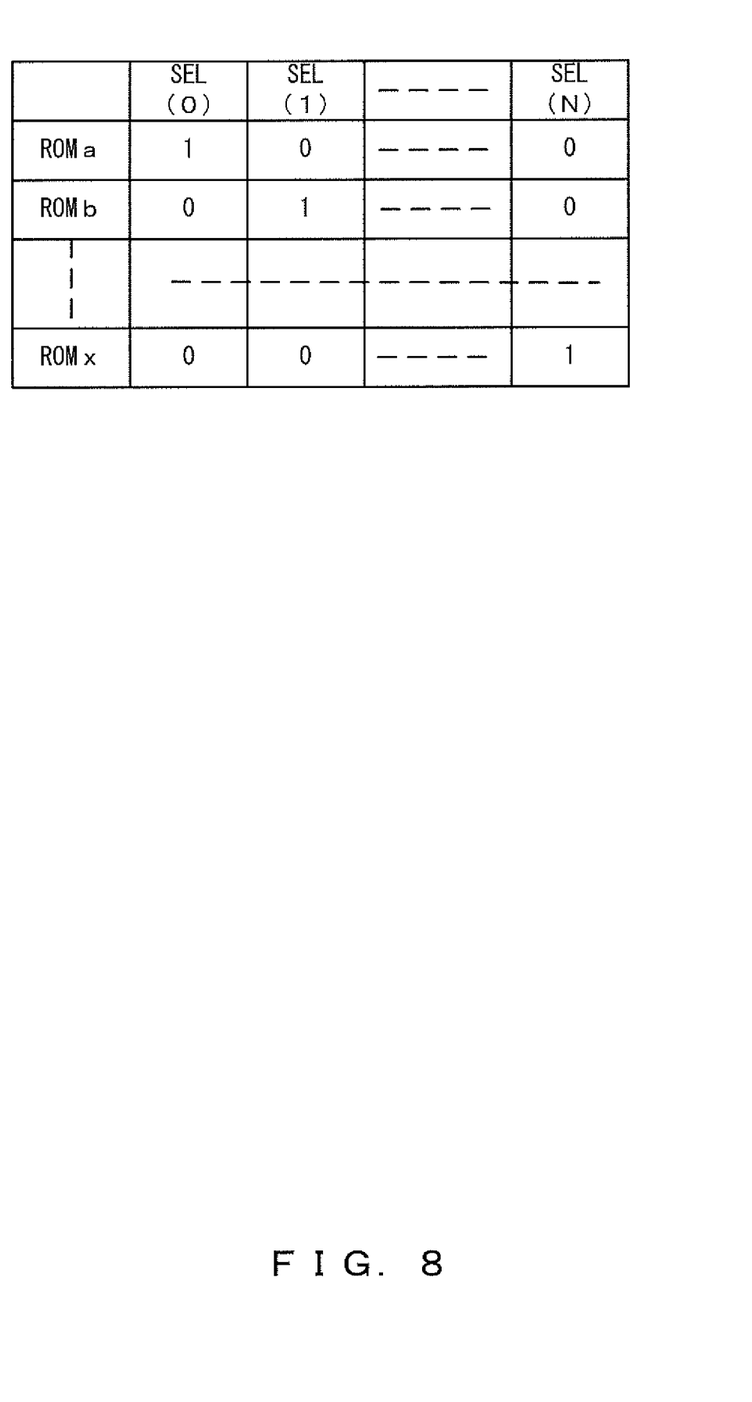
FIG. 8 illustrates a Read-Only Memory (ROM) that is selected in accordance with an output from each selector in the second embodiment.

FIG. 8 illustrates a ROM that is selected by the processor 200 in accordance with an output from each selector 214. For example, when only the selector (0) 214a outputs "1" from among the selectors 214, the ROM a221 is selected. Also, when only the selector (1) 214b outputs "1" from among the selectors 214, the ROM b222 is selected.

Explanations will be given for operations upon normal activation. As described above, when turning on of the power-source SW 13a is detected, the power-source IC 134 is turned on. At the start of the operation, only the selector (0) 214a outputs "1", and "1" is transmitted only to SEL(0) of the processor 200. The processor 200 specifies the ROM a221 as the memory to which the first program is to be loaded (referring to FIG. 8).

The processor 200 loads the first program from the ROM a221. When normal activation is achieved within a prescribed period of time (7.5 seconds for example), the processor 200 transmits WDT-Signal (watchdog signal) to the WDT 216.

When normal activation is impossible within a prescribed period of time (7.5 seconds for example), i.e., when the activation by the first program of the ROM a220 fails, the processor 200 refrains from transmitting WDT-Signal. When not receiving WDT-Signal within a prescribed period of time, the WDT 216 transmits RESET (reset signal) to the processor 200. At the same time, the WDT 216 transmits a switching signal to each selector 214 so that the reading-target memory is switched from the ROM a221 to the ROM b222. Specifically, the WDT 216 switches the output from the selector (0) 214a to the pull-down resistor, and switches the output from the selector (1) 214b to the pull-up resistor.

The processor 200 accesses the ROM b222 so as to load the second program.

When the second program achieves normal activation, the processor 200 remedies damage and a fault in the first program by using the second program.

When normal activation is impossible even through the second program, the processor 200 specifies a different ROM as the memory so as to load the third program.

In the second embodiment, similarly to the first embodiment, when activation is impossible within a prescribed period of time even by switching among a plurality of stored programs, the power-source IC 134 is turned off because a prescribed signal transmitted from the processor 200 to the OR2 gate 132 remains "L". This enables the prevention of battery consumption because the power source is disconnected after the elapse of a prescribed period of time when activation is impossible even through the second program.

A configuration is also possible in which a large-capacity NOR-type flash memory is used as the ROM a221, which is the main memory, and EEPROMs are used as the ROM b222 etc., which are sub memories. Using a program for the basic functions and the updating function as the second program and using EEPROMs as the ROM b222 etc., which are sub memories, can suppress an increase in the cost for the apparatus caused by providing a plurality of ROMs because a program for the basic functions and the updating function consumes less data and EEPROMs are inexpensive.

Also, the interchangeable medium 44 such as an SD card may be used as the ROM b222. An area of an SD card may be partitioned to set the area as an unrewritable area for storing the second program as an area of a sub memory. Using the interchangeable medium 44 as a sub memory can reduce additional costs for the ROMs. This configuration as well can reduce the influence on the capacity for recording image data by using a program for the updating function, which consumes less data, as the second program.

Third Embodiment

Figure 9:
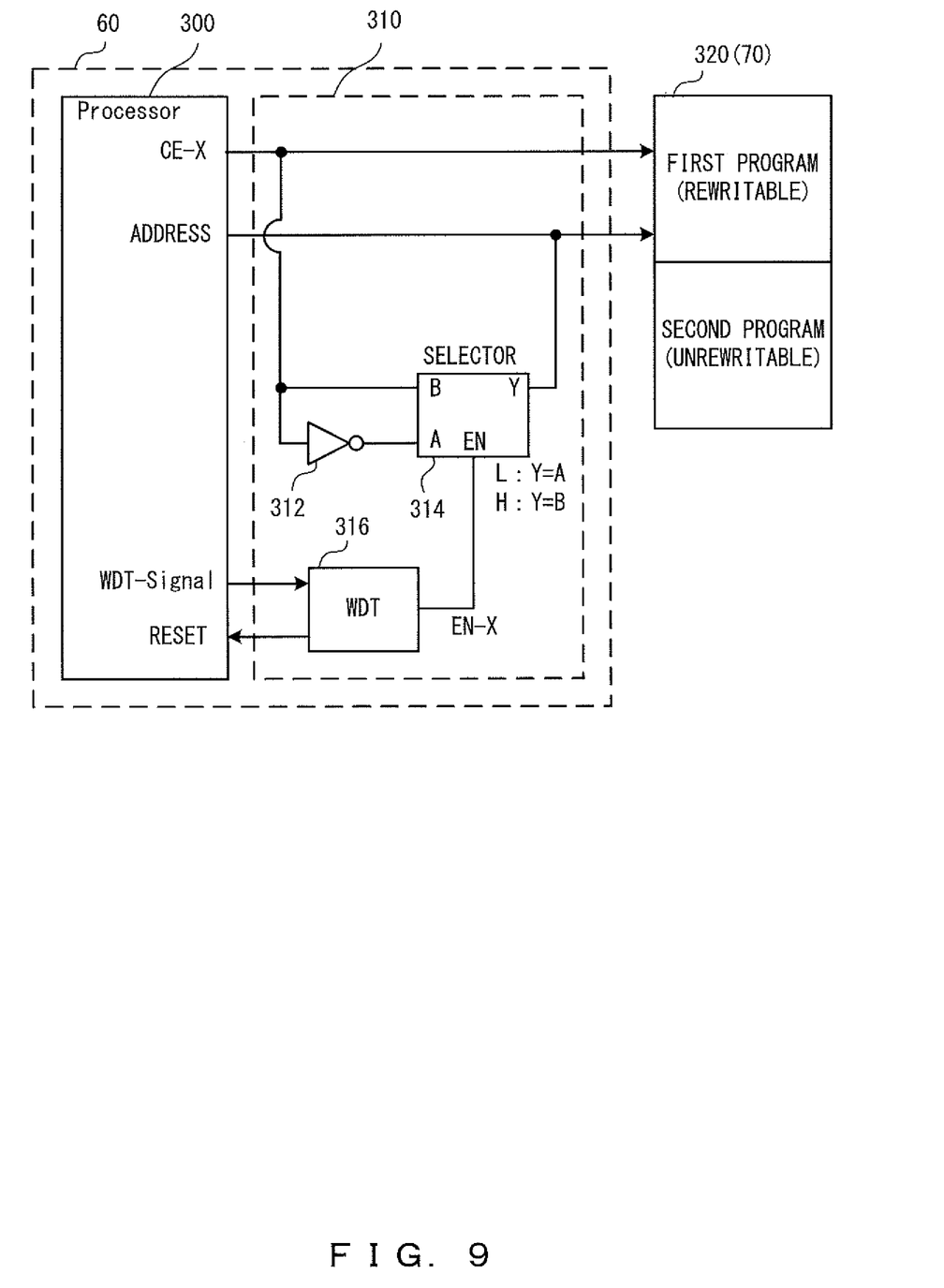
FIG. 9 illustrates an example of a configuration of a main control unit according to the third embodiment.

Explanations will be given for an activation process by a program according to the third embodiment by referring to FIG. 9. While the first embodiment selects a program from between programs stored in different memory chips, the third embodiment selects a program from among programs stored the same memory chip through switching. Note that the power-source control unit 42 according to the third embodiment has basically the same configuration as that illustrated in FIG. 3 (first embodiment), and thus will not be explained.

The main control unit 60 includes a processor 300 and a memory switching unit 310. Also, a ROM 320, which is the first recording medium 70, stores the first program for the normal operation and the second program for updating. In the ROM 320, the area storing the first program serves as the first storage unit and the area storing the second program serves as the second storage unit.

An output from the CE-X of the processor 300 is input to the CE (not illustrated) of the ROM 320. The memory switching unit 310 includes an inverter 312, a selector 314, and a watchdog timer (WDT) 316. The inverter 312 inverts an output from the CE-X of the processor 300, and outputs the result to the selector 314. Output Y from the selector 314 is added to the most significant bit of the address to the ROM 320.

When a prescribed period of time elapses without input of WDT-Signal (watchdog signal) from the processor 300, the WDT 316 applies RESET to the processor 300 and at the same time asserts EN-X, and maintains it until the input of the next WDT-Signal.

When the power source is turned on in response to the turning on of the power-source SW 13a, the processor 300 switches the CE-X from "H" to "L", and accesses the ROM 320. The EN-X output from the WDT 316 to the EN of the selector 314 is de-asserted, and "L" of the CE-X of the processor 300 is output from output Y of the selector 314.

"L" of the CE-X of the processor 300 is added to the most significant bit of the address to the ROM 320, and the most significant bit of the address becomes zero (L). The setting of the most significant bit of the address to zero causes the first program stored in the ROM 320 to be selected as the program that is to be loaded onto the processor 300. The processor 300 loads the selected first program, and performs activation. When normal activation is achieved, the processor 300 transmits WDT-Signal to the WDT 316 periodically.

When the activation through the first program fails, the processor 300 refrains from outputting WDT-Signal to the WDT 316. The WDT 316 transmits RESET to the processor 300, at the same time asserts the EN-X to the selector 314, and transmits a switching signal to the selector 314.

In accordance with the switching signal, the selector 314 switches inverted signal (H) to the output, inverted signal (H) resulting from the inverter 312 inverting the CE-X. "H" is added to the most significant bit of the address to the ROM 320. The setting of the most significant bit of the address to "1" causes the second program stored in the ROM 320 to be selected as the program that is to be loaded onto the processor 300. The processor 300 loads the selected second program and performs activation again.

When the second program achieves normal activation, the processor 300 transmits WDT-Signal to the WDT 316 periodically. The WDT 316 de-asserts the EN-X. After the activation through the second program, the processor 300 updates the first program through the second program so as to remedy damage and a fault in the first program.

The processor 300 according to the third embodiment enables the reactivation through the second program by accessing an area of the second program in the same chip even when the update by the first program fails and the activation is prevented. This enables update of a program without opening the case of the endoscope 10.

According to the third embodiment, similarly to the first embodiment, when activation is impossible within a prescribed period of time even by using the stored second program, the power-source control unit 42 halts the power-source IC 134 because a prescribed signal (not illustrated) transmitted from the processor 300 to the OR2 gate 132 remains "L". Thereby, the power source is disconnected after the elapse of a prescribed period of time when the activation is impossible even through the second program, and thus battery consumption can be prevented in the third embodiment as well.

Other Embodiments (1) Because the battery 40 may be removed when the cover SW 50a detects the opening of the cover 50 during the operation of the endoscope 10, if the processor 100 is accessing a memory (the first recording medium 70, the second recording medium 80, or the interchangeable medium 44), the access to the memory is immediately terminated.

For example, when the opening of the cover 50 is detected during a deletion process for a memory, the processor 100 deletes the file that is being deleted, and cancels the deletion of the remaining files. Also, if data is being written to a memory, the processor 100 completes the writing of the data that is being written, and terminates the process on the memory. This can prevent breakage of data that is being accessed.

A lock mechanism (not illustrated) for the battery 40 may be provided in the storage chamber so as to prevent the battery 40 from being removed accidentally. With such a lock mechanism, the power supply will surely continue even when the cover 50 is opened carelessly. Adding a lock mechanism for the battery 40 to the above process of terminating accesses to a memory upon the opening of the cover can prevent data breakage more securely. (2) As the endoscope 10 includes two media for recording an image, i.e., the interchangeable medium 44 and the second recording medium 80 as explained in FIG. 2, the second recording medium 80 (embedded memory) may automatically record image data when a shooting has consumed all the recording capacity of the interchangeable medium 44. (3) The endoscope 10 can record a video image and a still image in a memory (the interchangeable medium 44 and the second recording medium 80) together. However, it is important to prevent a video image from occupying a volume for a still image because still images are used as medical-case images of the endoscope 10. This is because the interchangeable medium 44 cannot be replaced during diagnoses.

Thus, a memory management device (not illustrated) of the main control unit 60 secures a prescribed ratio to the memory capacity exclusively for still images. For example, the memory management device secures 10 percent of the memory capacity exclusively for still images. The ratio exclusively for still images in the memory is for example a ratio that can securely enables the recording of still images for one medical case (20 still images for example). Thus, during a video shooting, a time that is a result of subtracting 10 percent, which is for still images, is displayed as the remaining volume as a time that allows video shootings. When the remaining volume becomes 10 percent in the memory, "0" is displayed as a time that allows video shootings, and the video shooting is halted.

Note that the present invention is not limited exactly to the above embodiments, and can be embodied in the implementation phases by modifying constitutional elements without departing from the spirit of the present invention. Also, it is possible to form various inventions by an appropriate combination of a plurality of constituent elements disclosed in the above embodiments. For example, all the constituent elements disclosed in the above embodiments may be combined appropriately. Further, constituent elements selected from different embodiments may be combined appropriately. It is as a matter of course that these various modification and application are possible without departing from the spirit of the present invention.

EXPLANATIONS OF LETTERS OR NUMERALS

10 ENDOSCOPE
12 LCD WITH A TOUCH PANEL
13a POWER-SOURCE SW
40 BATTERY
42 POWER-SOURCE CONTROL UNIT

44 INTERCHANGEABLE MEDIUM
50 COVER
50a COVER SW
60 MAIN CONTROL UNIT
70 FIRST RECORDING MEDIUM
80 SECOND RECORDING MEDIUM
100, 200, 300 PROCESSOR
110, 210, 310 MEMORY SWITCHING UNIT
112 OR GATE
114 214 314 SELECTOR
116 TIMER RESET UNIT
120 MAIN MEMORY
122 SUB MEMORY
130 TIMER IC
132 OR2 GATE
134 POWER-SOURCE IC
212 312 INVERTER
216 316 WDT
221 ROMa
222 ROMb
223 ROMx
320 ROM

The invention claimed is:

1. A battery-powered medical apparatus comprising:
a first memory configured to store a first program;
a second memory configured to store a second program, which is different than the first program; and
a processor configured to:
execute activation of the battery-powered medical apparatus by executing the first program stored in the first memory in response to receiving an activation instruction;
in response to the activation of the battery-powered medical apparatus failing to complete within a first predetermined period of time from start of executing activation by the first program, switch a program from the first program to the second program, and execute the activation of the battery-powered medical apparatus by executing the second program stored in the second memory; and
transmit a signal to a battery to control power supply from the battery and stop the power supply from the battery to the battery-powered medical apparatus in response to the activation executed by the second program failing to complete within a second predetermined period of time after executing the activation by the second program, such that the battery-powered medical apparatus does not receive power supply from the battery upon the second program failing to complete within the second predetermined period of time.

2. The battery-powered medical apparatus according to claim 1, wherein the processor is configured to transmit the signal to the battery to control the power supply from the battery so that electric power from the battery is continuously supplied to the battery-powered medical apparatus in response to the activation by the first program being completed within the first predetermined period of time, or in response to the activation by the second program being completed within the second predetermined period of time.

3. The battery-powered medical apparatus according to claim 1, wherein the processor is configured to rewrite at least part of the first program based on data stored in the second program in response to the activation by the second program being completed within the second predetermined period of time.

4. The battery-powered medical apparatus according to claim 1, wherein the second memory is removable from the battery-powered medical apparatus, and the second memory is part of a storage medium that stores image data.

5. The battery-powered medical apparatus according to claim 1, wherein a function implemented by the second program is part of a plurality of functions implemented by the first program.

6. The battery-powered medical apparatus according to claim 1, wherein the second program includes an update program.

7. The battery-powered medical apparatus according to claim 1, wherein the first memory and the second memory are provided in an identical memory chip.

8. An activation control method for a battery-powered medical apparatus including a processor configured to control power supply from a battery and switch a program that is executed by the processor, the method comprising:
first executing, by the processor, activation by a first program stored in a first memory in response to receiving an activation instruction;
in response to the activation of the battery-powered medical apparatus failing to complete within a first predetermined period of time from start of executing activation by the first program, switching, by the processor, a program from the first program to the second program stored in a second memory, and execute the activation of the battery-powered medical apparatus by executing the second program; and
transmitting, by the processor, a signal to the battery to control the power supply from the battery so that the power supply from the battery to the battery-powered medical apparatus is stopped in response to the activation by the second program failing to complete within a second predetermined period of time after executing the activation by the second program, such that the battery-powered medical apparatus does not receive power supply from the battery upon the second program failing to complete within the second predetermined period of time.

9. A battery-powered medical apparatus comprising:
a first memory configured to store a first program that controls normal operation of the battery-powered medical apparatus;
a second memory configured to store a second program, which is different than the first program, the second program controlling a limited operation compared to the first program that reduces functionality of the battery-powered medical apparatus; and
a processor configured to:
receive an activation instruction controlling the processor to perform activation of the battery-powered medical apparatus;
activate the battery-powered medical apparatus by executing the first program stored in the first memory in response to receiving the activation instruction;
upon elapse of a first predetermined period of time, which starts when the first program is executed, determine whether the activation of the battery-powered medical apparatus is complete;
in response to the activation of the battery-powered medical apparatus failing to complete within the first predetermined period of time, switch activation from the first program to the second program, and activate the battery-powered medical apparatus by executing the second program stored in the second memory;

upon elapse of a second predetermined period of time, which starts when the second program is executed, determine whether the activation of the battery-powered medical apparatus is complete;

in response to the battery-powered medical apparatus being activated within the second predetermined period of time, perform an update of the first program by rewriting at least a portion of the first program based on updated code stored in the second memory; and in response to the activation of the battery-powered medical apparatus failing to complete within the second predetermined period of time, stop performing the activation of the battery-powered medical apparatus, and transmit a signal to the battery to control power supply from a battery to stop the power supply to the battery-powered medical apparatus, such that the battery-powered medical apparatus does not receive power supply from the battery upon the second program failing to complete within the second predetermined period of time.

* * * * *